US00PP21892P3

(12) United States Plant Patent
Brugliera

(10) Patent No.: US PP21,892 P3
(45) Date of Patent: May 3, 2011

(54) ***DIANTHUS* PLANT NAMED 'FLORIAMETRINE'**

(50) Latin Name: *Dianthus caryophyllus*
Varietal Denomination: FLORIAMETRINE

(75) Inventor: Filippa Brugliera, Preston (AU)

(73) Assignee: International Flower Developments Pty Ltd. (AU)

( * ) Notice: Subject to any disclaimer, the term of this patent is extended or adjusted under 35 U.S.C. 154(b) by 0 days.

(21) Appl. No.: 12/291,865

(22) Filed: Nov. 14, 2008

(65) Prior Publication Data

US 2009/0139001 P1 May 28, 2009

Related U.S. Application Data

(60) Provisional application No. 60/988,293, filed on Nov. 15, 2007.

(51) Int. Cl.
*A01H 5/00* (2006.01)

(52) U.S. Cl. ..... Plt./272

(58) Field of Classification Search ..... Plt./272
See application file for complete search history.

(56) References Cited

U.S. PATENT DOCUMENTS 6,774,285 B1 * 8/2004 Brugliera et al. ..... 800/298

FOREIGN PATENT DOCUMENTS

WO WO 93/01290 1/1993
WO WO 96/36716 11/1996
WO WO 2004/020637 A1 3/2004

OTHER PUBLICATIONS

Dellaporta et al, "A Plant DNA Minipreparation: Version II," *Molecular Biology Reporter* 1(14):19-21, 1983.

Forkmann and Ruhnau, "Distinct Substrate Specificity of Dihydroflavonol 4-Reductase from Flowers of Petunia hybrida," *Z Naturforsch C.* 42c, 1146-1148, 1987.

Holton et al, "Cloning and expression of cytochrome P450 genes controlling flower colour," *Nature,* 366: 276-279, 1993.

Holton and Cornish, "Genetics and Biochemistry of Anthocyanin Biosynthesis," *Plant Cell* 7:1071-1083, 1995.

Johnson et al, "Cymbidium hybrida dihydroflavonol 4-reductase does not efficiently reduce dihydrokaempferol to produce orange pelargonidin-type anthocyanins,", *Plant Journal,* 19, 81-85, 1999.

Lazo et al, "A DNA Transformation-Competent Arabidopsis Genomic Library in Agrobacterium," *Bio/technology* 9:963-967, 1991.

Lu et al, "Agrobacterium-Mediated Transformation of Carnation (*Dianthus Caryophyllus* L.)," *Bio/Technology* 9: 864-868, 1991.

Mol et al, "How Genes Paint Flowers and Seeds," *Trends Plant Sci.* 3:212-217, 1998.

Sambrook et al, "Molecular Cloning: A Laboratory Manual," Cold Spring Harbor Laboratories, Cold Spring Harbor, NY, USA, 1989.

Tanaka and Mason, "Manipulation of Flower Colour by Genetic Engineering," Chapter 15, In *Plant Genetic Engineering,* Singh and Jaiwal (eds) SciTech Publishing LLC., USA, 1: 361-385, 2003.

Tanaka et al, "Genetic Engineering in Floriculture," *Plant Cell, Tissue and Organ Culture* 80: 1-24, 2005.

Tanaka and Brugliera, "Flower colour," Chapter 9, *In Flowering and Its Manipulation, Annual Plant Reviews* Ainsworth (ed), Blackwell Publishing, UK, 20: 201-239, 2006.

Winkel-Shirley, "Flavinoid Biosynthesis. A Colorful Model for Genetics, Biochemistry, Cell Biology, and Biotechnology," *Plant Physiol.* 126:485-493, 2001a.

Winkel-Shirley, "It Takes a Garden. How Work on Diverse Plant Species has Contributed to an Understanding of Flavonoid Metabolism," *Plant Physiol.* 127:1399-1404, 2001b.

* cited by examiner

*Primary Examiner*—Annette H Para
(74) *Attorney, Agent, or Firm*—Knobbe, Martens, Olson & Bear, LLP

(57) ABSTRACT

A new cultivar of *Dianthus* plant named 'FLORIAMETRINE' is characterized inter alia by altered inflorescence with respect to tissue and/or organelles including flowers or flower parts. This trait sets 'FLORIAMETRINE' apart from all other existing varieties, lines, strains or sports of *Dianthus.* In particular, *Dianthus* 'FLORIAMETRINE' has bright purple/violet flowers.

4 Drawing Sheets

Latin name of the genus and species claimed: *Dianthus Caryophyllus.*

Variety denomination: FLORIAMETRINE.

FIELD OF THE INVENTION

The present invention relates generally to the field of genetic modification of plants. More particularly, the present invention is directed to genetically-modified carnation plants expressing unique color phenotypes in selected parts of the plants.

BACKGROUND OF THE INVENTION

The flower or ornamental plant industry strives to develop new and different varieties of flowers and/or plants. An effective way to create such novel varieties is through the manipulation of flower color. Classical breeding techniques have been used with some success to produce a wide range of colors for almost all of the commercial varieties of flowers and/or plants available today. This approach has been limited, however, by the constraints of a particular species' gene pool and for this reason it is rare for a single species to have the full spectrum of colored varieties. For example, the development of novel colored varieties of plants or plant parts such as flowers, foliage and stems would offer a significant opportunity in both the cut flower and ornamental markets. In the flower or ornamental plant industry, the development of desired (including novel) colored varieties of carnation is of particular interest. This includes not only different colored flowers but also anthers and styles.

Flower color is predominantly due to three types of pigment: flavonoids, carotenoids and betalains. Of the three, the flavonoids are the most common and contribute a range of colors from yellow to red to blue. The flavonoid molecules that make the major contribution to flower color are the anthocyanins, which are glycosylated derivatives of cyanidin and its methylated derivative peonidin, delphinidin and its methylated derivatives petunidin and malvidin and pelargonidin. Anthocyanins are localized in the vacuole of the epidermal cells of petals or the vacuole of the sub epidermal cells of leaves.

The flavonoid pigments are secondary metabolites of the phenylpropanoid pathway. The biosynthetic pathway for the flavonoid pigments (flavonoid pathway) is well established, (Holton and Cornish, *Plant Cell* 7:1071-1083, 1995; Mol et al., *Trends Plant Sci.* 3:212-217, 1998; Winkel-Shirley, *Plant Physiol.* 126:485-493, 2001a; and Winkel-Shirley, *Plant Physiol.* 127:1399-1404, 2001b, Tanaka and Mason, In *Plant Genetic Engineering,* Singh and Jaiwal (eds.) SciTech Publishing Llc., USA, 1: 361-385, 2003, Tanaka et al., *Plant Cell, Tissue and Organ Culture* 80: 1-24, 2005, Tanaka and Brugliera, *In Flowering and Its Manipulation, Annual Plant Reviews* Ainsworth (ed.), Blackwell Publishing, UK, 20: 201-239, 2006). Three reactions and enzymes are involved in the conversion of phenylalanine to p-coumaroyl-CoA, one of the first key substrates in the flavonoid pathway. The enzymes are phenylalanine ammonia-lyase (PAL), cinnamate 4-hydroxylase (C4H) and 4-coumarate: CoA ligase (4CL). The first committed step in the pathway involves the condensation of three molecules of malonyl-CoA (provided by the action of acetyl CoA carboxylase (ACC) on acetyl CoA and $CO_2$) with one molecule of p-coumaroyl-CoA. This reaction is catalyzed by the enzyme chalcone synthase (CHS). The product of this reaction, 2',4,4',6', tetrahydroxy-chalcone, is normally rapidly isomerized by the enzyme chalcone flavanone isomerase (CHI) to produce naringenin. Naringenin is subsequently hydroxylated at the 3 position of the central ring by flavanone 3-hydroxylase (F3H) to produce dihydrokaempferol (DHK).

The pattern of hydroxylation of the B-ring of DHK plays a key role in determining petal color. The B-ring can be hydroxylated at either the 3', or both the 3' and 5' positions, to produce dihydroquercetin (DHQ) or dihydromyricetin (DHM), respectively. Two key enzymes involved in this part of the pathway are flavonoid 3'-hydroxylase (F3'H) and flavonoid 3', 5'-hydroxylase (F3'5'H), both members of the cytochrome P450 class of enzymes.

The production of colored anthocyanins from the dihydroflavonols (DHK, DHQ, DHM), involves dihydroflavonol-4-reductase (DFR) leading to the production of the leucoanthocyanidins. The leucoanthocyanidins are subsequently converted to the anthocyanidins, pelargonidin, cyanidin and delphinidin. These flavonoid molecules are unstable under normal physiological conditions and glycosylation at the 3-position, through the action of glycosyltransferases, stabilizes the anthocyanidin molecule thus allowing accumulation of the anthocyanins.

The substrate specificity shown by DFR can regulate the anthocyanins that a plant accumulates. Petunia and cymbidium DFRs do not reduce DHK and thus they do not accumulate pelargonidin-based pigments (Forkmann and Ruhnau, *Z Naturforsch C.* 42c, 1146-1148, 1987, Johnson et al., *Plant Journal,* 19, 81-85, 1999). Many important floricultural species including iris, delphinium, cyclamen, gentian, cymbidium are presumed not to accumulate pelargonidin due to the substrate specificity of their endogenous DFRs (Tanaka and Brugliera, 2006, supra).

In carnation, the DFR enzyme is capable of metabolizing two dihydroflavonols to leucoanthocyanidins which are ultimately converted through to anthocyanins pigments that are responsible for flower color. DHK is converted to leucopelargonidin, the precursor to pelargonidin-based pigments, giving rise to apricot to brick-red colored carnations. DHQ is converted to leucocyanidin, the precursor to cyanidin-based pigments, producing pink to red carnations. Carnation DFR is also capable of converting DHM to leucodelphinidin (Forkmann and Ruhnau, 1987 supra), the precursor to delphinidin-based pigments. However, naturally occurring carnation lines do not contain a F3'5'H enzyme and therefore do not synthesize DHM.

Nucleotide sequences encoding F3'5'Hs have been cloned (see International Patent Application No. PCT/AU92/00334 incorporated herein by reference and Holton et al., *Nature,* 366:276-279, 1993 and International Patent Application No. PCT/AU03/01111 incorporated herein by reference). These sequences were efficient in modulating 3', 5' hydroxylation of flavonoids in petunia (see International Patent Application No. PCT/AU92/00334 and Holton et al., 1993 supra), tobacco (see International Patent Application No. PCT/AU92/00334), carnations (see International Patent Application No. PCT/AU96/00296 incorporated herein by reference) and roses (see International Patent Application No. PCT/AU03/01111).

Carnations are one of the most extensively grown cut flowers in the world.

There are thousands of current and past cut-flower varieties of cultivated carnation. These are divided into three general groups based on plant form, flower size and flower type. The three flower types are standards, sprays and midis. Most of the carnations sold fall into two main groups, the standards and the sprays. Standard carnations are intended for cultivation under conditions in which a single large flower is required per stem. Side shoots and buds are removed (a process called disbudding) to increase the size of the terminal flower. Sprays and/or miniatures are intended for cultivation to give a large number of smaller flowers per stem. Only the central flower is removed, allowing the laterals to form a 'fan' of flowers.

Spray carnation varieties are popular in the floral trade, as the multiple flower buds on a single stem are well suited to various types of flower arrangements and provide bulk to bouquets used in the mass market segment of the industry.

Standard and spray cultivars dominate the carnation cut-flower industry, with approximately equal numbers sold of each type in the USA. In Japan, spray-type varieties account for 70% of carnation flowers sold by volume, whilst in Europe spray-type carnations account for approximately 50% of carnation flowers traded through out the Dutch auctions. The Dutch auction trade is a good indication of consumption across Europe.

Whilst standard and midi-type carnations have been successfully manipulated genetically to introduce new colors (Tanaka and Brugliera, 2006, supra; see International Patent Application No. PCT/AU96/00296), this has not been applied to spray carnations. There is an absence of blue color in color-assortment in carnation, only recently filled through the introduction of genetically-modified standard-type carnation varieties. However, standard-type varieties cannot be used for certain purposes, such as bouquets and flower arrangements where a large number of smaller carnation flowers are needed, such as hand-held arrangements, and small table settings.

One particular spray carnation which is particularly commercially popular is the Kortina Chanel line of carnations (*Dianthus caryophyllus* cv. Kortina Chanel). The variety has excellent growing characteristics and a moderate to good resistance to fungal pathogens such as *Fusarium*. There are a number of varieties which have been released as "sports" of Kortina Chanel. These include Kortina, Royal Red Kortina, Cerise Kortina and Dusty Kortina. However, before the advent of the present invention, purple/blue spray carnations were not available.

SUMMARY OF THE INVENTION

The following traits represent the characteristics of the new *Dianthus* cultivar 'FLORIAMETRINE'. These traits distinguish this cultivar from other commercial varieties. 'FLORIAMETRINE' may exhibit phenotypic differences with variations in environmental, climatic and cultural conditions, without any variance in genotype.

1. *Dianthus* 'FLORIAMETRINE' exhibits pronounced spray habit.
2. *Dianthus* 'FLORIAMETRINE' blooms profusely.
3. *Dianthus* 'FLORIAMETRINE' exhibits bright purple/violet flowers (RHS N78A).
4. *Dianthus* 'FLORIAMETRINE' exhibits green (RHS 137A) foliage.
5. At maturity, the height of the foliage mound of *Dianthus* 'FLORIAMETRINE' is 89 cm. The mature width about 15 to 18 cm.
6. *Dianthus* 'FLORIAMETRINE' is a perennial.
7. *Dianthus* 'FLORIAMETRINE' is suitable for use as a flowering plant in pots, containers, window boxes and the garden, but is primarily suited for the production of cut flowers.
8. *Dianthus* 'FLORIAMETRINE' is not hardy and is grown in a greenhouse.

BRIEF DESCRIPTION OF THE DRAWINGS

The accompanying color drawing illustrates the overall appearance of the new variety *Dianthus* 'FLORIAMETRINE' showing colors as true as reasonably possible to obtain in colored reproductions of this type. Colors in the drawing may differ from the color values cited in the detailed botanical description, which accurately describe the actual colors of the new variety 'FLORIAMETRINE'.

DETAILED DESCRIPTION OF THE PREFERRED EMBODIMENT

Figure 1:
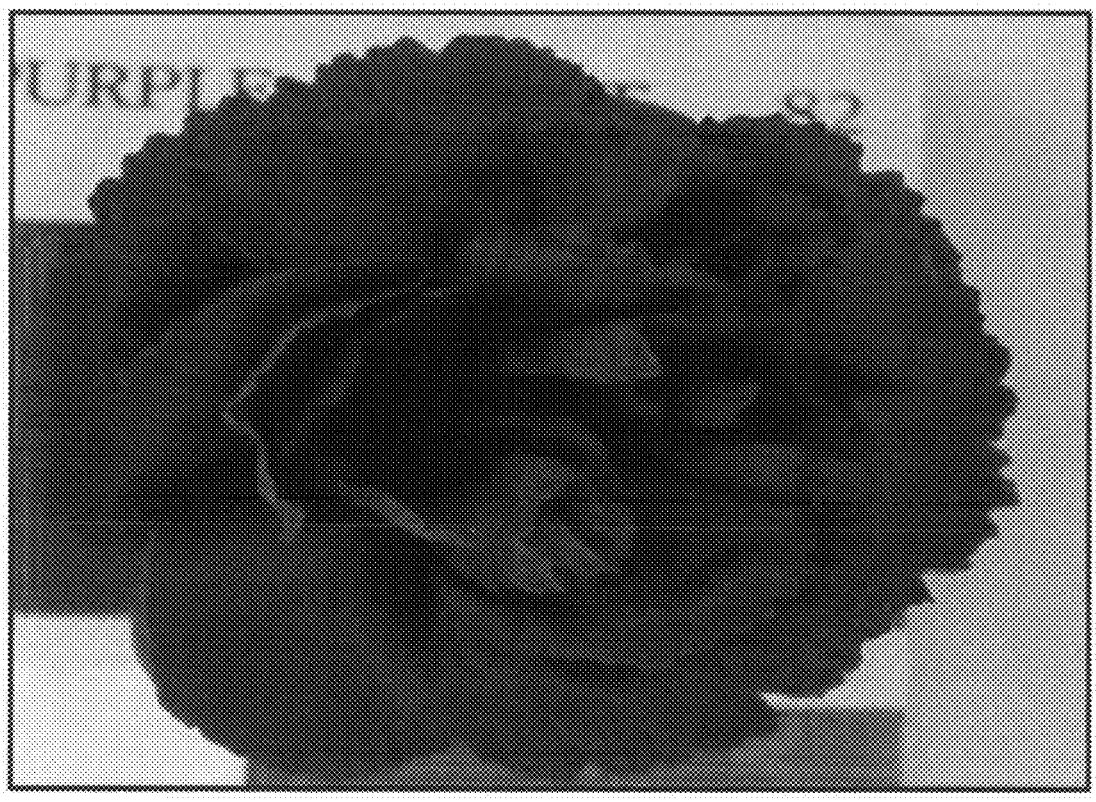
FIG. 1 is a photographic representation of the flower. Colors may appear different from the actual colors due to light reflection but are as accurate as possible by conventional photography.

The present invention relates to a new and distinct cultivar of carnation that is grown for use as a flowering plant for pots and containers. The new cultivar is known botanically as *Dianthus caryophyllus* and is referred to hereinafter by the cultivar name 'FLORIAMETRINE'.

'FLORIAMETRINE' is a complex transgenic plant comprising genetic sequences encoding at least two F3'5'H molecules and at least one DFR. The vector pCGP2442 used to transform meristematic cells contains a chimeric AmCHS 5': Salivia F3'5'H#47: petD8 3' gene in tandem with a petunia genomic DFR-A gene, a chimeric carnANS 5': BPF3'5'H#18: carnANS 3' gene and the 35S 5': SuRB selectable marker gene cassette of the plasmid pWTT2132.

The new variety originated in vitro by *Agrobacterium tumefaciens*-mediated transformation of meristematic cells of the Kortina Chanel (unpatented) carnation with the pCGP2442 vector at Florigene Pty Ltd., in Bundoora, Victoria, Australia. Cuttings of *Dianthus caryophyllus* cv. Kortina Chanel were obtained from Van Wyk and Son Flower Supply, Victoria or Propagation Australia, Queensland, Australia. Transgenic plants containing the chimeric AmCHS 5': SaliviaF3'5'H#47: petD8 3' gene in tandem with a petunia genomic DFR-A gene, and a chimeric carnANS 5': BPF3'5'H#18: carnANS 3' gene were successfully generated from the cells. In addition to these genes, the plants also contains genes for acetolactate synthase resistance (SuRB) transformation selection markers. The transformation and regeneration process is described in International Patent Application No. PCT/US92/02612; International Patent Application No. PCT/AU96/00296; and Lu et al., Bio/Technology 9: 864-868, 1991, the contents of each of which are incorporated by reference.

The primary focus of the carnation generation program was to produce new cultivars of carnations which exhibited a selected and desired purple/violet color in the spray background. The term 'FLORIAMETRINE' was selected because of its pronounced production of delphinidin or delphinidin-based molecules pigments.

The new variety was selected from a group of 74 transgenic lines of which only three produced flowers with a significant shift in color into the violet, purple/violet range. 'FLORIAMETRINE' is essentially similar to the parent in the morphological aspects of the flower, but can be further distinguished from the parent throughout the accumulation of pigment in the filaments and anthers of the flower. This is a new phenotype of the transgenic line. Some styles and anthers of 'FLORIAMETRINE' also have a shift in color to light purple, whereas the styles and anthers from flowers of the parent line were a cream-white color.

The new variety was originally selected in vitro as a regenerated shoot from a 'Kortina Chanel' carnation meristematic cell that had been transfected with *Agrobacterium tumefaciens* AGL0 (Lazo et al., Bio/technology 9:963-967, 1991) carrying the plasmid pCGP2442.

Asexual reproduction of the new cultivar was first accomplished in 2007 in a cultivated area of Bundoora, Victoria, Australia. The method of asexual propagation used was vegetative cuttings. Since that time the characteristics of the new cultivar have been determined stable and are reproduced true to type in successive generation of asexual reproduction.

BOTANICAL DESCRIPTION OF THE PLANT

The following is a detailed description of the new cultivar 'FLORIAMETRINE'. Data was collected from plants grown indoors in Bundoora, Victoria, Australia. The color determinations are in accordance with the 2001 edition of The Royal Horticultural Society (R.H.S.) Colour Chart except where general color terms of ordinary dictionary significance are used. Growing conditions are typical to other species, sports and lines of *Dianthus*.

Botanical classification: *Dianthus caryophyllus*.

Species: *Caryophyllus*.

Common name: Kortina Chanel.

Commercial classification: *Dianthus caryophyllus* 19907.

Type: Perennial.

Use: Used as a flowering plant for pots and containers.

Parentage: 'FLORIAMETRINE' is a transgenic plant that resulted from the transformation of *D. caryophyllus* with the transformation vector, pCGP2442.

TABLE 1

| Plant Description | |
|---|---|
| Bloom period | All year |
| Plant habit | Spray type carnation |
| Plant height | Average plant height at flowering—891 mm |
| Plant width | About 150 to 180 mm at flowering |
| Plant hardiness | Not tested for hardiness |
| Root system | Fine fibrous root system |
| Propagation | Vegetative propagation |
| Cultural requirements | Grown hydroponically in a greenhouse. Plants fertilized via drip irrigation system |
| Pests and diseases | Susceptible to known *Dianthus* pest and diseases |
| Time and Temperature needed to produce a rooted cutting | About 3 to 4 weeks to produce rooted cuttings, bench heat: 18-22° C., Air temp approximately 15 to 22° C. |
| Crop time | Average days to flowering: 107. |
| Stem shape | Cylindrical, Average stem length 782 mm, Average stem diameter at 5th node: 6 mm |
| Stem surface | Glabrous and glaucous |
| Stem color | 137B |
| Branching | Little branching from the axils of lower leaves |
| Internode length | Average length of 5th internode: 73 mm |
| Node color | 192D |
| Node dimensions | About 6 mm diameter and about 3 mm in length |
| **Foliage** | |
| Type | Evergreen |
| Shape | Linear |
| Division | Simple |
| Apex | Acute |
| Base | Decurrent |
| Venation | Not prominent |
| Margins | Entire |
| Attachment | Sheathing |
| Arrangement | Opposite and spiraling up stem |
| Surfaces | Glaucous |
| Leaf dimensions | 3rd leaf from flower, Average length: 40.5 mm, Average width: 7 mm |
| Leaf color | 137A |
| Fragrance | Absent |

TABLE 1-continued

| Flowers | |
|---|---|
| Inflorescence | Cymose |
| Flower type | Saliform, double and symmetrical |
| Flower dimensions (including calyx) | Average corolla height: 22.5 mm, Average calyx height: 32.5 mm |
| Fragrance | Absent |
| Bud color | 191B |
| Anthocyanin | Present |
| Bud dimensions | Average bud length: 26.4 mm, Average bud width: 9 mm |
| Bud shape | Cylindrical |
| Petals | Persistent, apopetalous, overlapping |
| Petal number | Average number of petals: 27 |
| Petal margin | Denate |
| Petal shape | Obtetoid |
| Petal surface | Glabrous |
| Petal dimensions | Average petal length: 47 mm, Average petal width: 22 mm |
| Ground color of blade | N78A |
| Color of band around centre | N78A |
| Color of middle of strap | 145C |
| Color of base of strap | 145D |
| Calyx dimensions | Average calyx length: 32.5 mm, Average calyx diameter at apex: 14.5 mm |
| Calyx color | 138B |
| Anthocyanin | Absent |
| Sepals | Average number of sepals: 6 |
| Fused or Unfused | Unfused |
| Sepal color | 138B |
| Anthocyanin | Absent |
| Peduncle dimensions | Average peduncle length: 33.6 mm, Average peduncle width: 2 mm |
| Peduncle color | 138A |
| Peduncle surface | Glaucous |
| Epicalyx | Present |
| Bracts | 1 pair in number (2 individual bracts) |
| Bracts dimensions | About 3 mm by about 20 mm |
| Bract color | 138A |
| Anthacyanin | Absent |
| Bracteoles | 1 or 2 pair |
| Dimensions | About 3 mm by about 25 mm |
| Anthocyanin | Absent |
| Stipules | Absent |
| Stipules dimensions | N/A |
| Stipule color | N/A |
| Anthacyanin | N/A |
| Lastiness of flowers | 14 days |
| **Reproductive Organs** | |
| Stamens | Average number of stamens: 10 |
| Stamen dimensions | Average length of stamen: 21.5 mm |
| Stamen color | Upper: N80C, Lower: N155B |
| Anther number | Average of normal anthers: 2, Average of abnormal anthers: 6 |
| Anther attachment | Dorsifixed |
| Anther color | N80C |
| Anther dimensions | Average anther length: 1.84 mm, Average anther width: 0.68 mm |
| Pollen | Little pollen |
| Pistil | One that divides into 2 above the ovary |
| Pistil dimensions | Average pistil length: 34 mm |
| Styles | Average No: 2, Average length: 26 mm |
| Style color | N155B |
| Stigma number | Single |
| Stigma shape | A single stigma |
| Stigma color | N155B |
| Height above petals | Stigma does not protrude above petals |
| Ovary postion | Superior |
| Ovary dimensions | Average ovary height: 8 mm, Average ovary width: 5.5 mm |
| Ovary shape | Obovoid |

TABLE 1-continued

| | |
|---|---|
| Ovary color | Upper: 145A, Lower: 155A |
| Seed | Absent |

TABLE 2

| | Floriametrine | Kortina Chanel control |
|---|---|---|
| | Description | |
| Bloom period | All year | All year |
| Plant habit | Spray type carnation | Spray type carnation |
| Plant height | Average plant height at flowering —895 mm | Average plant height at flowering —853 mm |
| Plant width | 150 to 180 mm at flowering | 150 to 180 mm at flowering |
| Plant hardiness | Not tested for hardiness | Not tested for hardiness |
| Root system | Fine fibrous root system | Fine fibrous root system |
| Propagation | Vegetative propagation | Vegetative propagation |
| Cultural requirements | Grown hydroponically in a greenhouse. Plants fertilized via drip irrigation system | Grown hydroponically in a greenhouse. Plants fertilized via drip irrigation system |
| Pests and diseases | Susceptible to known *Dianthus* pest and diseases | Susceptible to known *Dianthus* pest and diseases |
| Time and Temperature needed to produce a rooted cutting | 3 to 4 weeks to produce rooted cuttings, bench heat: 18-22° C., Air temp approx. 15 to 22° C. | 3 to 4 weeks to produce rooted cuttings, bench heat: 18-22° C., Air temp approx. 15 to 22° C. |
| Crop time | Average days to flowering: 107. | Average days to flowering: 108 |
| Stem shape | Cylindrical, Ave stem length 782 mm, Ave stem diameter at $5^{th}$ node: 6 mm | Cylindrical, Ave stem length 713 mm, Ave. stem diameter at $5^{th}$ node: 6.7 mm |
| Stem surface | Glabrous and glaucous | Glabrous and glaucous |
| Stem color | 137B | 137B |
| Branching | Little branching from the axils of lower leaves | Little branching from the axils of lower leaves |
| Internode length | Average length of $5^{th}$ internode: 73 mm | Average length of $5^{th}$ internode: 73 mm |
| Node color | 192D | 192D |
| Node dimensions | 6 mm diameter and 3 mm in length | 6 mm diameter and 3 mm in length. |
| | Foliage | |
| Type | Evergreen | Evergreen |
| Shape | Linear | Linear |
| Division | simple | simple |
| Apex | Acute | Acute |
| Base | Decurrent | Decurrent |
| Venation | Not prominent | Not prominent |
| Margins | Entire | Entire |
| Attachment | Sheathing | Sheathing |
| Arrangement | Opposite and spiraling up stem | Opposite and spiraling up stem |
| Surfaces | Glaucous | Glaucous |
| Leaf dimensions | $3^{rd}$ leaf from flower, Ave length: 40.5 mm, Ave width: 7 mm | $3^{rd}$ leaf from flower, Ave length: 39 mm, Ave width: 8 mm |
| Leaf color | 137A | 137A |
| Fragrance | Absent | Absent |
| | Flowers | |
| Inflorescence | Cymose | Cymose |
| Flower type | Saliform, double and symmetrical | Saliform, double and symmetrical |
| Flower dimensions including calyx) | Ave. corolla height: 22.5 mm, Ave calyx height: 32.5 | Ave corolla height: 23.5 mm, Ave. calyx height: 31.5 mm |
| Fragrance | Absent | Absent |
| Bud color | 191B | 191B |
| Anthocyanin | Present | Present |
| Bud dimensions | Ave bud length: 26.4 mm, Ave bud width: 9 mm | Ave bud length: 24.9 mm, Ave bud width: 9.9 mm |
| Bud shape | Cylindrical | Cylindrical |
| Petals | Persistent, apopetalous, overlapping | Persistent, apopetalous, overlapping |
| Petal number | Ave number of petals: 27 | Ave number of petals: 32 |
| Petal margin | Denate | Denate |
| Petal shape | Obtetoid | Obtetoid |
| Petal surface | Glabrous | Glabrous |
| Petal dimensions | Ave petal length: 47 mm, Ave petal width: 22 mm | Ave petal length: 47 mm, Ave petal width: 22 mm |
| Ground color of blade | N78A | 65A |
| Color of band around centre | N78A | 65A |
| Color of middle of strap | 145C | 145C |
| Color of base of strap | 145D | 145D |
| Calyx dimensions | Ave calyx length: 32.5 mm, Ave calyx diameter at apex: 14.5 mm | Ave calyx length: 31.5 mm, Ave calyx diameter at apex: 14.9 mm |
| Calyx color | 138B | 138B |
| Anthocyanin | Absent | Absent |
| Sepals | Ave number of sepals: 6 | Ave number of sepals: 5.4 |
| Fused or Unfused | Unfused | Unfused |
| Sepal color | 138B | 138B |
| Anthocyanin | absent | absent |
| Peduncle dimensions | Ave peduncle length: 33.6 mm, Ave peduncle width: 2 mm | Ave peduncle length: 45.2 mm, Ave peduncle width: 2.4 |
| Peduncle color | 138A | 138A |
| Peduncle surface | Glaucous | Glaucous |
| Epicalyx | Present | Present |
| Bracts | 1 pair in number (2 individual bracts) | 1 pair in number (2 individual bracts) |
| Bracts dimensions | 3 mm × 20 mm | 3 mm × 20 mm |
| Bract color | 138A | 138A |
| Anthacyanin | absent | absent |
| Bracteoles | 1 or 2 pair | 1 or 2 pair |
| Dimensions | 3 mm × 25 mm | 3 mm × 25 mm |
| Anthocyanin | Absent | Absent |

The *Dianthus* 'FLORIAMETRINE' is now described by the following non-limiting Examples.

EXAMPLE 1

GENERATION OF *DIANTHUS* 'FLORIAMETRINE'

In order to increase the levels of delphinidin-based anthocyanins and therefore increase the chance of violet/purple/blue color in the Kortina Chanel spray carnation flowers, a novel construct was prepared that included the use of two F3'5'H chimeric genes and a petunia DFR gene.

The DFR genomic fragments used in this application were isolated from petunia. The petunia DFR enzyme is only capable of using DHQ and DHM as a substrate, but not DHK (Holton and Cornish, 1995 supra). This ensures that most or all of the anthocyanidin produced is delphinidin.

The F3'5'H coding sequences in the chimeric genes used in the new construct were from pansy (carnANS 5': BP F3'5'H #18: carnANS 3' in pCGP2205) and salvia (AmCHS 5': Salvia F3'5'H #47: petD8 3' in pCGP2122) as these represent the two expression cassettes that were the most efficient in producing the highest levels of delphinidin in the Kortina Chanel spray carnation.

Preparation of the Transformation Vector, pCGP2442

Figure 2:
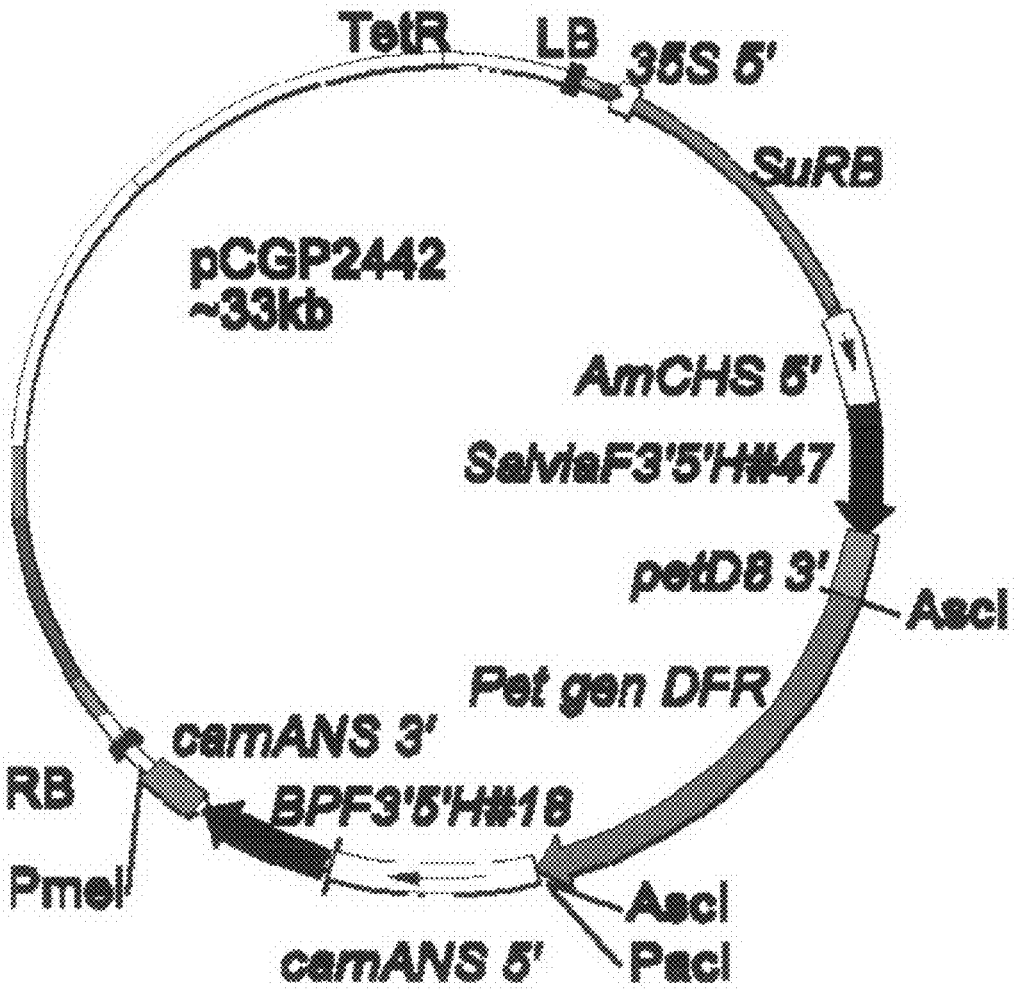
FIG. 2 is a diagrammatic representation of the binary plasmid pCGP2442. Selected restriction endonuclease sites (AscI, PacI, PmeI) are marked. Abbreviations include LB=Left Border from *A. tumefaciens* Ti plasmid; RB=Right Border region from *A. tumefaciens* Ti plasmid; TetR=tetracycline resistance gene complex.

The transformation vector pCGP2442 (FIG. 2) contains a chimeric AmCHS: Salvia F3'5'H#47: petD8 3' gene in tandem with a petunia genomic DFR-A gene, a chimeric carnANS 5': BPF3'5'H#18: carnANS 3' gene and the 35S 5': SuRB selectable marker gene cassette of the plasmid pWTT2132 (see International Patent Application No. PCT/AU03/01111 incorporated herein by reference).

*Agrobacterium tumefaciens* Strains and Transformations

The disarmed *Agrobacterium tumefaciens* strain used was AGL0 (Lazo et al., 1991 supra).

Plasmid DNA was introduced into the *Agrobacterium tumefaciens* strain AGL0 by adding 5 μg of plasmid DNA to 100 μL of competent AGL0 cells prepared by inoculating a 50 mL LB culture (Sambrook et al., Molecular Cloning: A Laboratory Manual, Cold Spring Harbor Laboratories, Cold Spring Harbor, N.Y., USA, 1989) and incubation for 16 hrs with shaking at 28° C. The cells were then pelleted and resuspended in 0.5 mL of 85% (v/v) 100 mM $CaCl_2$/15% (v/v) glycerol. The DNA-*Agrobacterium* mixture was frozen by incubation in liquid $N_2$ for 2 minutes and then allowed to thaw by incubation at 37° C. for 5 minutes. The DNA/bacterial mix was then placed on ice for a further 10 minutes. The cells were then mixed with 1 mL of LB (Sambrook et al., 1989 supra) media and incubated with shaking for 16 hrs at 28° C. Cells of *A. tumefaciens* carrying the plasmid were selected on LB agar plates containing appropriate antibiotics such as 50 μg/mL tetracycline or 100 μg/mL gentamycin. The confirmation of the plasmid in *A. tumefaciens* was done by restriction endonuclease mapping of DNA isolated from the antibiotic-resistant transformants.

Plant transformations were as described in International Patent Application No. PCT/US92/02612 or International Patent Application No. PCT/AU96/00296 or Lu et al., *Bio/Technology* 9: 864-868, 1991 each incorporated herein by reference.

Cuttings of *Dianthus caryophyllus* cv. Kortina Chanel were obtained from Van Wyk and Son Flower Supply, Victoria or Propagation Australia, Queensland, Australia.

EXAMPLE 2

DETECTION OF THE SURB CHIMERIC GENE FROM THE TRANSFORMATION VECTOR PGP2442 IN *DIANTHUS* 'FLORAMETRINE' PLANTS

Figure 3:
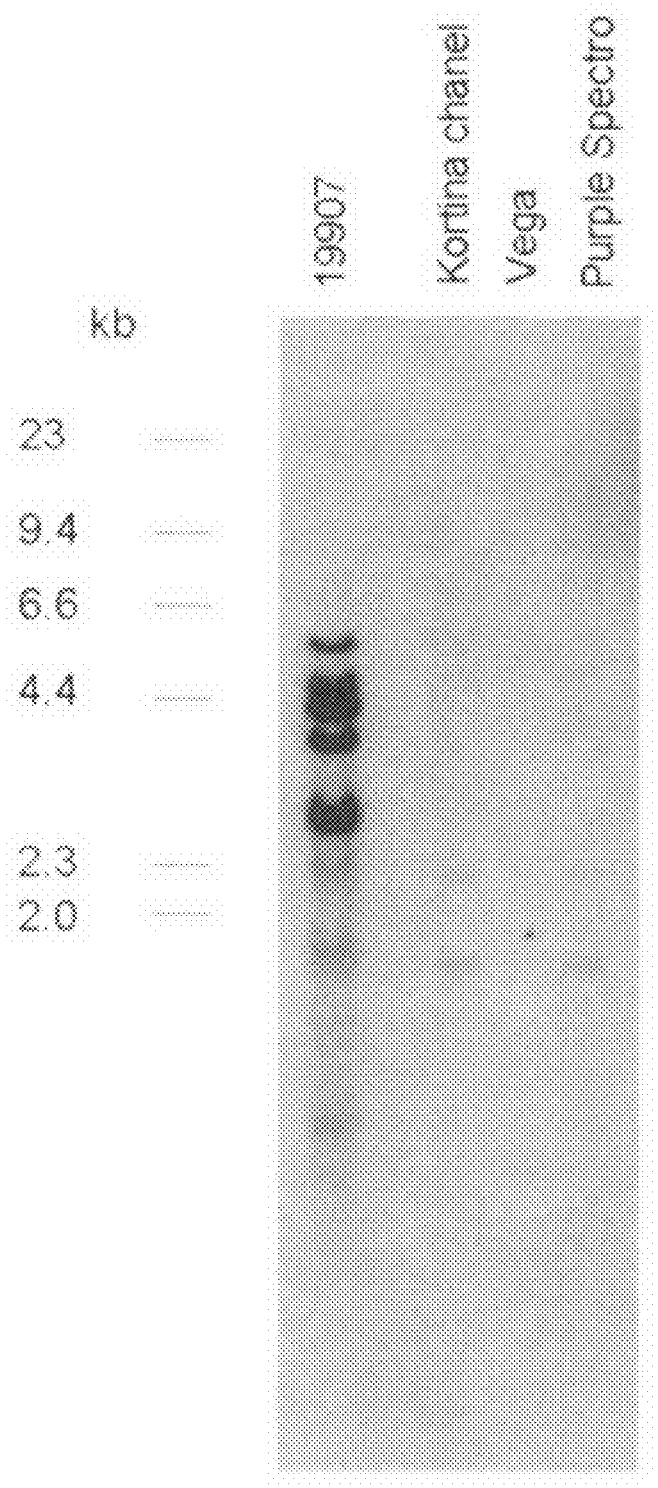
FIG. 3 is a photographic representation of a high resolution scan of a Southern blot autoradiograph showing 10 μg of EcoRI-treated genomic DNA from the transgenic carnation line 19907, in comparison to 10 μg of EcoRI-treated genomic DNA from the carnation lines Kortina Chanel, Vega and Purple Spectro, hybridized with the NtALS probe.
Figure 4:
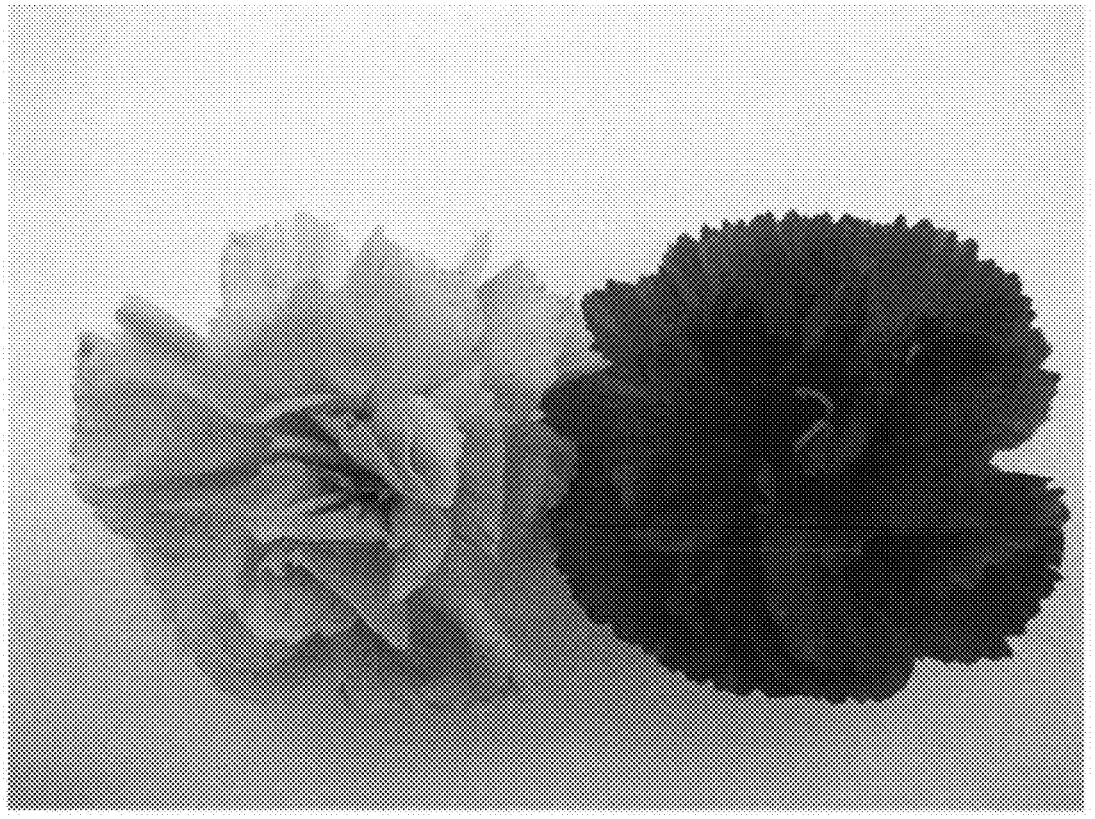
FIG. 4 is a photographic representation of the 'Kortina Chanel' control on the left and the cultivar 'FLORIAMETRINE' on the right.

In order to determine stable transformation of *Dianthus caryophyllus* with the T-DNA from the transformation vector pCGP2442, transgenic plants were analyzed by Southern blot. The results are shown in FIG. 3.

Preparation of Genomic DNA and Southern Analysis

Genomic DNA was isolated from leaf tissues as described by Dellaporta et al., *Molecular Biology Reporter* 1(14):19-21, 1983. The genomic DNA (10 μg) was digested for 48 hours using 120 units of the restriction endonuclease EcoRI at 37° C. DNA fragments were separated by electrophoresis through a 0.8% w/v agarose gel. The DNA was transferred to Hybond NX membrane (Amersham) as described (Sambrook et al., 1989 supra).

The following samples were analyzed:

1. HindIII-treated λDNA standard markers (size range: 23.13, 9.42, 6.56, 4.36, 2.32, 2.03 kb),
2. 10 μg of EcoRI-treated genomic DNA from transgenic carnation line 19907 (FLORIAMETRINE),
3. 10 μg of EcoRI-treated genomic DNA from non-transgenic carnation parental line, Kortina Chanel,
4. 10 μg of EcoRI-treated genomic DNA from non-transgenic carnation line, Vega; and
5. 10 μg of EcoRI-treated genomic DNA from non-transgenic carnation line, Purple Spectro.

Following electrophoresis, the gel was prepared for blotting by a 15 minute depurination step in 0.25 M HCl, two 20 minute washes in denaturing solution (1.5 M NaCl, 0.5 M NaOH) and two 20 minute washes in neutralization solution (0.5 M Tri-HCl, pH 7.5, 0.48 M HCl, 1.5 M NaCl). DNA was capillary transferred to Hybond-NX nylon membrane (Amersham Biosciences, UK) in 20×SSC (3 M NaCl, 0.3 M Tris-Na citrate, pH 7.0).

Preparation of Probes

A probe corresponding to a 770 bp fragment of the ALS (acetolactate synthase) gene from *Nicotiana tabacum* (NtALS) was used for Southern blot analysis. The probe fragment was originally generated by PCR and subsequently sub-cloned into an amplification vector (pBluescript II, Stratagene, USA), given a reference number (pCGP1651) and the fragment sequenced. After confirmation of the correct sequence, the DNA fragment was isolated from the source plasmid using the restriction endonuclease HindIII. The fragment was separated by 1% w/v agarose gel electrophoresis and purified using the MinElute Gel Extraction kit and protocol (Qiagen, Australia).

32P-Labeling of DNA Probes

DNA fragments (25-50 ng) were labeled with 50 μCi of [α-32P]-dCTP (PerkinElmer Life and Analytical Sciences, USA) using a Decaprime kit (Ambion, USA). Unincorporated [α-$^{32}$P]-dCTP was removed by chromatography on Sephadex G-50 (Fine) columns. The labeled probe fragment was counted using a BioScan radioisotope counter (QC:4000 XER, BioScan, USA).

Hybridization and Detection

Membranes were pre-hybridized in 10 mL hybridization buffer 50% v/v deionized formamide, 1 M NaCl, 1% w/v SDS and 10% w/v dextran sulfate) at 42° C. for 1 hr. Once denatured, 10,000,000 dpm of $^{32}$P -labeled probe was added to the hybridization solution and hybridization was continued at 42° C. for a further 16 hours. Membranes were washed twice in low stringency buffer (2×SSC, 1% w/v SDS) at 65° C. for 30 minutes. Membranes were exposed to Kodax BioMax MS X-Ray film (Kodak, USA) with an intensifying screen at −70° C. for 16 hours. The exposed films were automatically developed using a Curix 60 X-ray developer (AGFR-Gevaert Group, Belgium).

What is claimed is:

1. A new and distinct cultivar or *Dianthus* plant named 'FLORIAMETRINE' as described and illustrated herein.

* * * * *